(12) United States Patent  (10) Patent No.: US 7,395,714 B2
Georgeson et al.  (45) Date of Patent: *Jul. 8, 2008

(54) MAGNETICALLY ATTRACTED INSPECTING APPARATUS AND METHOD USING A BALL BEARING

(75) Inventors: Gary E. Georgeson, Federal Way, WA (US); Michael D. Fogarty, Auburn, WA (US); Daniel J. Wright, Mercer Island, WA (US)

(73) Assignee: The Boeing Company, Chicago, IL (US)

( * ) Notice: Subject to any disclaimer, the term of this patent is extended or adjusted under 35 U.S.C. 154(b) by 274 days.

This patent is subject to a terminal disclaimer.

(21) Appl. No.: 10/943,088

(22) Filed: Sep. 16, 2004

(65) Prior Publication Data

US 2006/0055399 A1    Mar. 16, 2006

(51) Int. Cl.
*G01N 9/24* (2006.01)
(52) U.S. Cl. .............................. 73/634; 73/639; 73/643; 73/644
(58) Field of Classification Search ................ 73/643, 73/634, 635, 639, 640, 641, 644, 618, 619, 73/620, 633
See application file for complete search history.

(56) References Cited

U.S. PATENT DOCUMENTS

| | | | |
|---|---|---|---|
| 3,956,938 A * | 5/1976 | Carrico | 73/728 |
| 3,958,451 A | 5/1976 | Richardson | |
| 4,167,880 A | 9/1979 | George | |
| 4,311,052 A | 1/1982 | Jeffras et al. | |
| 4,468,619 A * | 8/1984 | Reeves | 324/220 |
| 4,536,690 A * | 8/1985 | Belsterling et al. | 318/687 |
| 4,728,941 A * | 3/1988 | Andrejasich | 340/620 |

(Continued)

FOREIGN PATENT DOCUMENTS

DE    198 26 759 C1    12/1999

(Continued)

OTHER PUBLICATIONS

*Automated Ultrasonic Scanning System (AUSS®), Mobile Automated Scanner (MAUS®)* http://www.engineeringatboeing.com/mfgquality/quality/automatedsystems.html, Jun. 21, 2004, 4 pages.

(Continued)

*Primary Examiner*—Hezron E. Williams
*Assistant Examiner*—Jacques M. Saint-Surin
(74) *Attorney, Agent, or Firm*—Alston & Bird LLP

(57) ABSTRACT

An apparatus and method for inspecting a structure are provided which include probes with sensing elements and are disposed proximate the opposite surfaces of a structure, where only one of the probes need be driven. A tracking probe may be magnetically coupled to a driven probe and move in coordination therewith. Ring magnets may be used in the driven and tracking probes to provide the magnetic coupling and align sensing elements disposed in the centers of the ring magnets. The probes include ball bearings such as ball and socket bearings for supporting the structure and maintaining the desired orientation and spacing of the probes relative to the structure. A fluid, such as water or pressurized air, may be used as a couplant between an ultrasonic transducer and the structure. A water column skirt may be used to with a probe employing ball bearings for support.

36 Claims, 6 Drawing Sheets

U.S. PATENT DOCUMENTS

| | | | |
|---|---|---|---|
| 4,774,842 | A | 10/1988 | Kollar |
| 5,050,703 | A | 9/1991 | Graff et al. |
| 5,148,414 | A | 9/1992 | Graff et al. |
| 5,164,921 | A | 11/1992 | Graff et al. |
| 5,297,408 | A * | 3/1994 | Yoshida .................. 72/12.7 |
| 5,421,203 | A | 6/1995 | Graff et al. |
| 5,585,564 | A | 12/1996 | Brunty et al. |
| 5,593,633 | A | 1/1997 | Dull et al. |
| 5,677,490 | A | 10/1997 | Gunther et al. |
| 5,902,935 | A | 5/1999 | Georgeson et al. |
| 6,484,583 | B1 * | 11/2002 | Chennell et al. ............ 73/623 |
| 6,516,668 | B2 | 2/2003 | Havira et al. |
| 6,539,642 | B1 * | 4/2003 | Moriyasu et al. ............ 33/551 |
| 6,658,939 | B2 | 12/2003 | Georgeson et al. |
| 6,722,202 | B1 | 4/2004 | Kennedy et al. |
| 6,748,791 | B1 | 6/2004 | Georgeson et al. |
| 6,843,131 | B2 | 1/2005 | Graff et al. |
| 6,931,931 | B2 | 8/2005 | Graff et al. |
| 2003/0154801 | A1 | 8/2003 | Georgeson |
| 2003/0183002 | A1 * | 10/2003 | Burger et al. ............... 73/313 |
| 2003/0210027 | A1 | 11/2003 | Pedigo et al. |
| 2004/0103721 | A1 | 6/2004 | Georgeson |
| 2004/0237653 | A1 | 12/2004 | Graff et al. |
| 2006/0053891 | A1 * | 3/2006 | Georgeson et al. ............ 73/624 |
| 2006/0053892 | A1 * | 3/2006 | Georgeson et al. ............ 73/634 |

FOREIGN PATENT DOCUMENTS

| | | | |
|---|---|---|---|
| JP | 407181141 A | * | 7/1995 |
| JP | 9229911 A | | 9/1997 |
| JP | 2003232378 | * | 8/2007 |

OTHER PUBLICATIONS

*Non Destructive Testing*, http://www.aascworld.com/ndt-ttu.htm, Aug. 19, 2004, 3 pages.

*Inspection of In-Service Composite-Honeycomb Structures*, Aerospace Application Note, Rev.: Jan. 2002, R/D Tech.

*Probe Catalog 2003-2004*, Thru-Transmission Ultrasonics, NDT Engineering Corporation, R/D Tech Company, pp. 1-11.

*Air-Coupled Ultrasonic Inspection*, http://www.qmi-inc.com/AIRSCAN.htm, Aug. 19, 2004, 3 pages.

*AIRSCAN® Transducer Specifications*, http://www.qmi-inc.com/Airscan%20TX%20Specifications.htm, Aug. 19, 2004, 18 pages.

U.S. Appl. No. 10/752,890, filed Jan. 7, 2004, In re: Bossi et al., entitled *Non-Destructive inspection Device for Inspecting Limited-Access Features of a Structure*.

U.S. Appl. No. 10/734,452, filed Dec. 12, 2003, In re: Bossi et al., entitled *Ultrasonic Inspection Device for Inspecting Components at Preset Angles*.

* cited by examiner

MAGNETICALLY ATTRACTED INSPECTING APPARATUS AND METHOD USING A BALL BEARING

CROSS-REFERENCE TO RELATED APPLICATIONS

The contents of applications filed concurrently herewith and entitled "Magnetically Attracted Inspecting Apparatus and Method Using a Fluid Bearing," "Alignment Compensator for Magnetically Attracted Inspecting Apparatus and Method," "Apparatus and Method for Area Limited-Access Through Transmission Ultrasonic Inspection," and "End Effector Inspection Apparatus and Method" are incorporated by reference in their entireties. The contents of U.S. Pat. No. 6,722,202 to Kennedy are incorporated by reference in its entirety.

FIELD OF THE INVENTION

The present invention relates generally to an apparatus and method for inspecting a structure and, more particularly, to using a ball bearing with a magnetically coupled inspection probe.

BACKGROUND

Non-destructive inspection (NDI) of structures involves thoroughly examining a structure without harming the structure or requiring significant disassembly of the structure. Non-destructive inspection is typically preferred to avoid the schedule, labor, and costs associated with removal of a part for inspection, as well as avoidance of the potential for damaging the structure. Non-destructive inspection is advantageous for many applications in which a thorough inspection of the exterior and/or interior of a structure is required. For example, non-destructive inspection is commonly used in the aircraft industry to inspect aircraft structures for any type of internal or external damage to or flaws in the structure. Inspection may be performed during manufacturing of a structure and/or once a structure is in-service. For example, inspection may be required to validate the integrity and fitness of a structure for continued use in manufacturing and future ongoing use in-service. However, access to interior surfaces is often more difficult or impossible without disassembly, such as removing a part for inspection from an aircraft.

Among the structures that are routinely non-destructively tested are composite structures, such as composite sandwich structures and other adhesive bonded panels and assemblies. In this regard, composite structures are commonly used throughout the aircraft industry because of the engineering qualities, design flexibility and low weight of composite structures, such as the stiffness-to-weight ratio of a composite sandwich structure. As such, it is frequently desirable to inspect composite structures to identify any flaws, such as cracks, voids or porosity, which could adversely affect the performance of the composite structure. For example, typical flaws in composite sandwich structures, generally made of one or more layers of lightweight honeycomb or foam core material with composite or metal skins bonded to each side of the core, include disbonds which occur at the interfaces between the core and the skin or between the core and a septum intermediate skin.

Various types of sensors may be used to perform non-destructive inspection. One or more sensors may move over the portion of the structure to be examined, and receive data regarding the structure. For example, a pulse-echo (PE), through transmission (TT), or shear wave sensor may be used to obtain ultrasonic data, such as for thickness gauging, detection of laminar defects and porosity, and/or crack detection in the structure. Resonance, pulse echo or mechanical impedance sensors may be used to provide indications of voids or porosity, such as in adhesive bondlines of the structure. High resolution inspection of aircraft structure is commonly performed using semi-automated ultrasonic testing (UT) to provide a plan view image of the part or structure under inspection. While solid laminates may be inspected using one-sided pulse echo ultrasonic (PEU) testing, composite sandwich structures typically require through-transmission ultrasonic (TTU) testing for high resolution inspection. In through-transmission ultrasonic inspection, ultrasonic sensors such as transducers, or a transducer and a receiver sensor, are positioned facing the other but contacting opposite sides of the structure to be inspected such as opposite surfaces of a composite material. An ultrasonic signal is transmitted by at least one of the transducers, propagated through the structure, and received by the other transducer. Data acquired by sensors, such as TTU transducers, is typically processed by a processing element, and the processed data may be presented to a user via a display.

The non-destructive inspection may be performed manually by technicians who typically move an appropriate sensor over the structure. Manual scanning generally consists of a trained technician holding a sensor and moving the sensor along the structure to ensure the sensor is capable of testing all desired portions of the structure. In many situations, the technician must repeatedly move the sensor side-to-side in one direction while simultaneously indexing the sensor in another direction. For a technician standing beside a structure, the technician may repeatedly move the sensor right and left, and back again, while indexing the sensor between each pass. In addition, because the sensors typically do not associate location information with the acquired data, the same technician who is manually scanning the structure must also watch the sensor display while scanning the structure to determine where the defects, if any, are located in the structure. The quality of the inspection, therefore, depends in large part upon the technician's performance, not only regarding the motion of the sensor, but also the attentiveness of the technician in interpreting the displayed data. Thus, manual scanning of structures is time-consuming, labor-intensive, and prone to human error.

Semi-automated inspection systems have been developed to overcome some of the shortcomings with manual inspection techniques. For example, the Mobile Automated Scanner (MAUS®) system is a mobile scanning system that generally employs a fixed frame and one or more automated scanning heads typically adapted for ultrasonic inspection. A MAUS system may be used with pulse-echo, shear wave, and through-transmission sensors. The fixed frame may be attached to a surface of a structure to be inspected by vacuum suction cups, magnets, or like affixation methods. Smaller MAUS systems may be portable units manually moved over the surface of a structure by a technician. However, for through-transmission ultrasonic inspection, a semi-automated inspection system requires access to both sides or surfaces of a structure which, at least in some circumstances, will be problematic, if not impossible, particularly for semi-automated systems that use a fixed frame for control of automated scan heads.

Automated inspection systems have also been developed to overcome the myriad of shortcomings with manual inspection techniques. For example, the Automated Ultrasonic Scanning System (AUSS®) system is a complex mechanical scanning system that employs through-transmission ultrasonic inspection. The AUSS system can also perform pulse echo inspections, and simultaneous dual frequency inspections. The AUSS system has robotically controlled probe arms that must be positioned proximate the opposed surfaces of the structure undergoing inspection with one probe arm moving an ultrasonic transmitter along one surface of the structure, and the other probe arm correspondingly moving an ultrasonic receiver along the opposed surface of the structure. Conventional automated scanning systems, such as the AUSS-X system, therefore require access to both sides or surfaces of a structure which, at least in some circumstances, will be problematic, if not impossible, particularly for very large or small structures. To maintain the ultrasonic transmitter and receiver in proper alignment and spacing with one another and with the structure undergoing inspection, the AUSS-X system has a complex positioning system that provides motion control in ten axes. This requirement that the orientation and spacing of the ultrasonic transmitter and receiver be invariant with respect to one another and with respect to the structure undergoing inspection is especially difficult in conjunction with the inspection of curved structures.

Furthermore, manual, semi-automated, and automated scanning systems typically are limited in the size of a structure that can be inspected, generally limited to areas just a few meters square and typically limited to much smaller areas, although some larger, more complicated systems are available. Stiffness and weight limitations often restrict the distance a manual, semi-automated, or automated system may be able to extend inspection devices over a structure for inspection. Thus, large composite structures may not be capable of complete inspection. For example, contemporary inspection methods are not well suited for inspecting a Sea Launch payload fairing with a diameter of approximately four meters, a cylindrical length of approximately five meters, and an overall length of over twelve meters.

To increase the rate or speed at which the inspection of a structure is conducted, the scanning system may include ultrasonic probes that have arrays of ultrasonic transmitters and receivers. As such, the inspection of the structure can proceed more rapidly and efficiently, thereby reducing the costs associated with the inspection. Unfortunately, the use of arrays of ultrasonic transmitters and receivers is generally impractical during the scanning of curved structures, such as large-scale curved composite structures. While some array systems may be capable of scanning gently sloping structures, more complicated curved structures typically are impractical to inspect with an array, such as requiring that the array system be flexible. In this regard, conventional ultrasonic scanning systems for inspecting large-scale curved composite parts use water jets to provide water between the surface of the structure undergoing inspection and the ultrasonic transmitter or receiver to effectively couple ultrasonic signals into and out of the structure. In instances in which the ultrasonic probes include an array of ultrasonic transmitters or receivers, it has been difficult to design a corresponding water jet array that does not produce significant interference or crosstalk between the elements of the array.

Accessibility to the structure requiring inspection and particular features thereof is one consideration in choosing a non-destructive inspection device. Access to the structure requiring inspection may be so limited that a manual inspection by a technician or a semi-automated or automated system is not possible, typically due to systems requiring access to exterior and interior surfaces of the structure to be inspected. For example, the backside of an inlet duct for an Unmanned Combat Air Vehicle (UCAV) or an F-35 has limited access for inspection. Alignment and positioning of sensors such as transducers is similarly complicated by accessibility to the structure such as inaccessibility to one side of a composite structure.

Accordingly, a need exists for an improved non-destructive inspection device and method to inspect a structure.

SUMMARY OF THE INVENTION

An improved apparatus and method for inspecting a structure, such as a composite structure and, especially a curved composite structure, provides ball bearing support for magnetically coupled inspection probes. An inspection apparatus or method using an alignment compensator of the present invention may advantageously improve inspection of a structure, such as continuous inspection of a large area of a structure, by maintaining alignment and positioning of sensing transducers and/or receivers. The method and apparatus of the present invention use probes including respective sensing elements, such as ultrasonic transducers, that are disposed proximate the opposed surfaces of a structure. Only one of the probes need be driven. Thus, the method and apparatus of the present invention are advantageously adapted to inspect structures in which one surface of the structure is relatively inaccessible. Additionally, embodiments of the method and apparatus of the present invention are capable of operating in an ultrasonic array mode, even in conjunction with the inspection of curved structures, thereby increasing the speed and efficiency with which such structures may be inspected and correspondingly reducing the cost associated with the inspection. Further, embodiments of the method and apparatus of the present invention permit the probes to contact and ride along the respective surfaces of the structure. Thus, embodiments of the present invention may reduce the necessary sophistication of the motion control system that is otherwise required by conventional scanning systems to maintain the ultrasonic probes in a predefined orientation and at a predefined spacing from the respective surface of a structure undergoing inspection and may maintain alignment between the probes or the sensors of the probes.

The apparatus of the present invention includes a driven probe disposed proximate a first surface of the structure and a tracking probe disposed proximate an opposed second surface of the structure. The driven probe is moved along the first surface of the structure in response to the application of motive force, such as by means of a robotic arm or other positioning system. In contrast, the tracking probe generally moves along the second surface of the structure in response to the movement of the driven probe and independent of the application of any other motive force. Thus, the tracking probe generally passively follows the movement of the driven probe such that the tracking probe need not be engaged by a robotic arm or other positioning system. The tracking probe can therefore be disposed on the backside or other surface of a structure that is relatively inaccessible.

To facilitate the coordinated movement of the tracking probe in conjunction with the driven probe, both the driven probe and the tracking probe advantageously include a magnet which draws the driven and tracking probes toward the first and second surfaces of the structure, respectively. Ring magnets may be used in the driven and tracking probes to provide magnetic coupling of the two probes to the respective surfaces of the structure. Additionally, the magnetic attraction between the magnets of the driven and tracking probes causes the tracking probe to be moved over the second surface of the structure in response to corresponding movement of the driven probe.

The driven probe includes a sensing element for inspecting a structure as the driven probe is moved along the first surface of the structure. While the sensing element may be an x-ray detector, a camera or the like, the sensing element is typically an ultrasonic transducer. Typically, the tracking probe also includes a sensing element, such as an ultrasonic transducer. The ultrasonic transducers may be an ultrasonic transmitter, an ultrasonic receiver, or both. For a probe having a ring magnet, a sensor, such as an ultrasonic transducer, may be positioned at the center of the ring magnet; thus, as the ring magnets of the probes align the two probes on respective surfaces of the structure, the sensors of the probes are also aligned at the centers of the ring magnets.

To facilitate the coupling of the ultrasonic signal between the ultrasonic transducer of the driven probe and the structure, a couplant may be disposed between the ultrasonic transducer and the respective surfaces of the structure. While air or water jets may be used as a couplant, the driven probe of one advantageous embodiment may instead include an inlet for fluid that is pumped or bubbled between the ultrasonic transducer and the first surface of the structure. In this regard, the driven probe may include a housing in which the magnet and the ultrasonic transducer are disposed, and which defines the inlet. The fluid may be in fluid communication with that portion of the ultrasonic transducer that faces the first surface of the structure. Thus, the fluid that is pumped or bubbled between the ultrasonic transducer and the first surface of the structure may facilitate coupling of the ultrasonic signals produced by the ultrasonic transducer into the structure. Likewise, the tracking probe may include an inlet for fluid that is pumped or bubbled between the ultrasonic transducer of the tracking probe and the second surface of the structure. In this regard, the tracking probe can also include a housing in which the magnet and the ultrasonic transducer are disposed, and which defines the inlet. Again, the fluid may be in fluid communication with that portion of the ultrasonic transducer of the tracking probe that faces the second surface of the structure. Thus, ultrasonic signals emerging from the structure may be effectively coupled to the ultrasonic transducer of the tracking probe by the fluid that is pumped or bubbled therebetween. By pumping or bubbling fluid between the ultrasonic transducers and the respective surfaces of the structure, water jets are not required such that the ultrasonic transducers of the driven and tracking probes may include arrays of ultrasonic transducers, thereby permitting the rate at which the structure is inspected to be increased and the associated inspection cost accordingly decreased.

According to one advantageous embodiment, the driven probe includes a bearing contact, such as a ball and socket bearing, for contacting the first surface of the structure, supporting or suspending the driven probe, maintaining orientation and spacing of the probe with respect to the surface, and reducing the frictional drag of the driven probe on the surface of the structure being inspected to permit smooth translation of the driven probe across the surface of the structure. Thus, the driven probe may translate along the first surface of the structure with the orientation of the driven probe relative to the first surface of the structure and the spacing of the driven probe relative to the first surface of the structure being maintained by the bearing contact between the driven probe and the first surface of the structure without requiring the complex motion control systems used by conventional scanning systems. Likewise, the tracking probe may include a bearing contact, such as a ball and socket bearing, for contacting the second surface of the structure, supporting the tracking probe, maintaining orientation and spacing of the probe with respect to the surface, and reducing the frictional drag of the tracking probe on the surface of the structure being inspected to permit smooth translation of the tracking probe across the surface of the structure and magnetic coupling with the driven probe. Like the driven probe, the tracking probe may therefore be maintained in a predefined orientation and at a predefined spacing relative to the second surface of the structure without requiring the complex motion control systems used by conventional scanning systems. This independence from the motion control systems used by conventional scanning systems may further reduce the cost of the apparatus of the present invention and permit the tracking probe to be moved in a controlled fashion over a surface of a structure that is relatively inaccessible for a robotic arm or other conventional motion control system. The probes may contact the surface of the structure using a ball and socket bearing. When using ball and socket bearings, a fluid, such as water or air, may be used as a couplant between an ultrasonic transducer of a probe and a surface of the structure, such as bubbling water from an inlet in a probe. Other fluids, such as a gases, liquids, or gas-liquid mixtures, may be used as couplants between a sensor of a probe and a surface being inspected. A probe employing ball bearings for support and translation of the probe and employing a liquid, such as water, as a couplant between an ultrasonic transducer of a probe and a surface of the structure may include a water column skirt to form a path between the face of the transducer proximate the surface of the structure under inspection and the surface of the structure. A water column skirt may be a flexible cowling made from or covered with a low-friction substance, such as a Teflon® material available from E.I. DuPont Nemours and Company of Wilmington, Del., disposed on the surface of the probe proximate the surface of the part under inspection and around liquid flow channels on the surface of the probe proximate the surface of the structure under inspection.

According to another aspect of the present invention, a method of inspecting a structure is provided. In this regard, the driven probe is positioned proximate the first surface of the structure, and the tracking probe is positioned proximate the opposed second surface of the structure. For example, driven and tracking probes may be in contact with the first and second surfaces of the structure, respectively, thereby simplifying the alignment and spacing of the probes relative to the respective surfaces of the structure and relative to the other probe or a sensor of the other probe. The method of inspecting a structure also establishes magnetic attraction between the driven and tracking probes such that the driven and tracking probes are drawn toward the first and second surfaces of the structure, respectively. The driven probe is then moved along the first surface of the structure, such as in response to the application of a motive force by a robotic arm or other positioning system. The movement of the driven probe and the magnetic attraction between the driven and tracking probes causes the tracking probe to be correspondingly moved along the second surface of the structure. Advantageously, the tracking probe moves along the second surface of the structure independent of the application of any motive force. Thus, the tracking probe may be disposed proximate a relatively inaccessible surface of a structure since the movement of the tracking probe need not be controlled by a robotic arm or other positioning system.

As the driven probe is moved along the first surface of the structure, ultrasonic signals are transmitted to the structure by the ultrasonic transducer of one of the probes and are received by the ultrasonic transducer of the other probe following propagation through the structure. The driven and/or tracking probes are advantageously spaced from the respective surface by bearing contact. For example, ball and socket bearings may be used for bearing contact between the probes and the structure to contact the surface of the structure to permit smooth translation of the probes along the surfaces of the structure. To effectively couple the ultrasonic signals between the driven and tracking probes and the structure, a fluid may be pumped or bubbled between the sensors of the driven and tracking probes and the first and second surfaces of the structure, respectively, while ultrasonic signals are transmitted into and received from the structure. Additionally, or alternatively, air or water jets may be used to provide air or water respectively as the couplant.

These and other characteristics, as well as additional details, of the present invention are further described in the Detailed Description with reference to these and other embodiments.

BRIEF DESCRIPTION OF THE DRAWING(S)

Having thus described the invention in general terms, reference will now be made to the accompanying drawings, which are not necessarily drawn to scale, and wherein:

DETAILED DESCRIPTION

The present invention will be described more fully with reference to the accompanying drawings. Some, but not all, embodiments of the invention are shown. The invention may be embodied in many different forms and should not be construed as limited to the embodiments described. Like numbers and variables refer to like elements and parameters throughout the drawings.

I. Ball Bearing Magnetically Coupled Inspection Probes

Figure 1A:
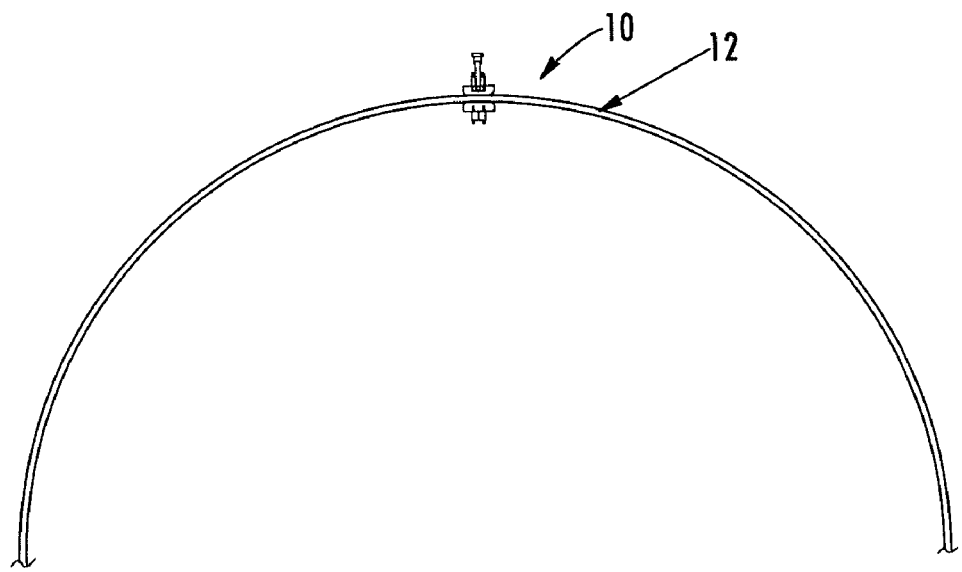
FIG. 1A is a schematic diagram of two probes of an apparatus according to embodiments of the present invention magnetically coupled to surfaces of a structure for inspection.
Figure 1B:
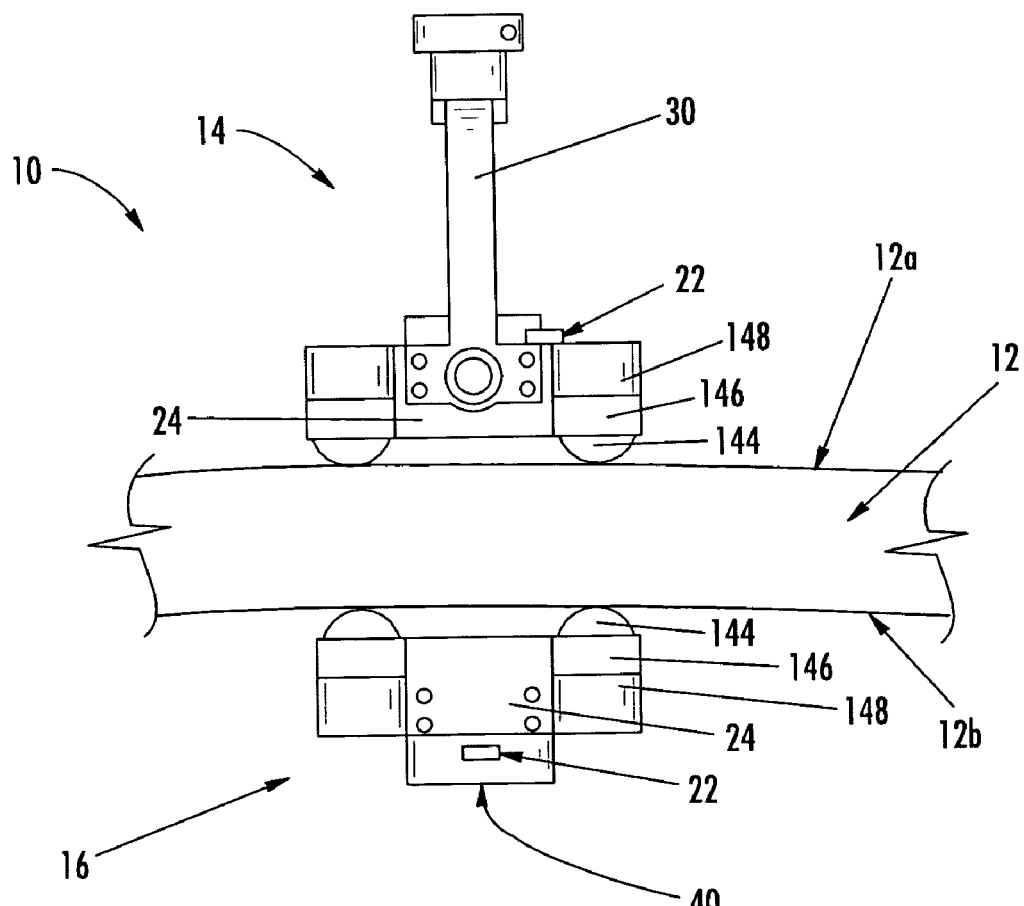
FIG. 1B is a magnified schematic diagram of two probes of an apparatus according to embodiments of the present invention magnetically coupled to surfaces of a structure for inspection.

Referring now to FIGS. 1A and 1B, an apparatus 10 for inspecting a structure 12 according to one embodiment of the present invention is depicted. The apparatus can inspect a variety of structures formed of various materials. Since the apparatus relies to some extent upon the establishment of magnetic fields through the structure, however, the structure is preferably non-magnetic, that is, the structure preferably has no magnetic permeability. Structures that may be inspected with an embodiment of an inspection device of the present invention may include, but are not limited to, composites, non-ferromagnetic metals (e.g. aluminum alloy, titanium alloy, or aluminum or titanium hybrid laminates such as GLARE or Ti/Gr), and polymers. It should be noted that the surfaces, and the material therebetween such as intermediate surfaces commonly referred to as septums, which collectively define the material through which the driven and tracking probes are magnetically coupled, preferably comprise a non-ferromagnetic material because the magnetic coupling between the probes would be diminished or eliminated by a ferromagnetic material located between the actuating portion and the inspecting portions.

While a portion of a relatively simple but large structural panel 12 is depicted during the course of an inspection in FIGS. 1A and 1B, a structure may be any myriad of shapes and/or sizes. In addition, the structure that is inspected may be used in a wide variety of applications, including in vehicular applications, such as in conjunction with aircraft, marine vehicles, automobiles, space craft and the like, as well as other non-vehicular applications, such as in conjunction with buildings and other construction projects. Moreover, the structure may be inspected prior to assembly or following assembly, as desired.

An apparatus 10 of the present invention includes a driven probe 14 disposed proximate a first surface 12a of the structure 12 and a tracking probe 16 disposed proximate an opposed second surface 12b of the structure. Embodiments of the present invention may be used with an inspection device similar to that disclosed in U.S. Pat. No. 6,722,202 to Kennedy directed to magnetically attracted probes for inspection of a structure, which is incorporated by reference. The shape and size of an inspection probe, and housing thereof, which may employ the present invention is not limited to the specific embodiments described and disclosed herein or in the U.S. Pat. No. 6,722,202 patent or referenced co-pending applications, but may be any shape or size capable of operating in accordance with the present invention. As described below, the driven and tracking probe may be disposed in contact with the first and second surfaces of the structure, respectively. Driven and tracking probes are advantageously initially positioned in alignment so as to be directly opposed one another or otherwise in positional correspondence with one another, as shown in FIGS. 1A and 1B. As shown in FIGS. 1A and 1B, for example, this alignment provides a linear relationship between the probes 14, 16 such that one probe is not translated or offset laterally across the surface of the structure 12 from the other probe. As described below, this positional relationship or correspondence between the driven and tracking probes is maintained as the probes are moved along the respective surfaces of the structure.

Each probe 14, 16 includes a ring magnet 118 that may be disposed within a housing 24, 124. The magnets of the probes magnetically attract the driven and tracking probes toward the respective surfaces of the structure 12. Using probes with ring magnets on opposing surfaces of a structure also aligns the two probes with respect to the other. By comparison, magnetically coupled inspecting probes using bar magnets, flat magnets, cylindrical magnets, and the like, require configurations of magnets and/or ferromagnetic materials to align the probes. Such configurations typically cannot provide the flexibility of ring magnets which may permit a tracking probe to rotate freely with respect to a magnetically coupled driven probe while maintaining alignment of ultrasonic transducers located within the center of the ring magnets in the driven and tracking probes. Magnetically coupled probes employing embodiments of the present invention may alternatively, or in addition, use magnets and/or ferromagnetic materials to provide alignment and/or magnetic attraction between probes. While each probe may include any number of magnets, each probe need only include one ring magnet which reduces the size, weight, cost, and complexity of the probes. Magnets of the illustrated embodiments may be ring magnets formed of neodymium iron boron, which have advantageously have greater magnetic flux (around 12,000 gauss) than standard ceramic or ferrite magnets (around 3,900 gauss). Further embodiments of the invention may include magnets of different material, such as Samarium Cobalt or Alnico and/or electromagnets or other magnetic coupling means. The term "magnet" as used herein is inclusive of electromagnets. The probes of the present invention may further comprise magnetic shunting mechanisms to control the magnetic flux of the magnetic couplings, a non-limiting example being rare earth metal switched magnetic devices disclosed in U.S. Pat. No. 6,180,928. While various types of ring magnets may be used, the driven and tracking probes of one embodiment include permanent ring magnets, such as NdFeB ring magnets. The size of ring magnets for both the driven and tracking probes may be dependent, at least in part, upon the weight of the respective probes, the thickness of the structure undergoing inspection, and the material that forms the structure undergoing inspection. For example, a ring magnet of a probe may be 4 inches in diameter and 1 inch in height with a magnetic flux of 3.9k Gauss across the surface of the ring magnet if the magnet is a standard ferrite ring magnet or 12k Gauss if the magnet is an NdFeB ring magnet. Additionally, driven and tracking probes may include ring magnets having either the same or different sizes. Different size ring magnets may help to maintain alignment of the probes and may permit adjustment of the weight of a probe, such as to reduce the weight of a probe which hangs beneath the surface of a structure.

Although ring magnets may be used independently to positionally align probes of embodiments of the present invention, rotational alignment of probes may be enhanced, such as by incorporating at least one additional magnet or ferromagnetic material to at least one of the probes. Selecting the magnetic polarity of at least one additional magnet of one of the probes to be such that the respective additional magnet is repelled by one or more of the magnets of the other probe or attracted by one or more of the magnets or a ferromagnetic material of the other probe. For example, if one of the probes includes ferromagnetic material, such as a plug of ferromagnetic material, the other probe may include an additional magnet positioned such that the probes are properly positioned with respect to one another when the ferromagnetic plug and the additional magnet are aligned since the ferromagnetic plug and the additional magnet of the other probe will be attracted to one another when these elements are properly aligned to position the probes with rotational alignment. Similarly, if the probes each include two additional magnets, where the two additional magnets of each probe have opposite polarities, when the probes are misaligned, the additional magnets of the probes would be repelled and produce a rotation of the probes until the additional magnets of the probes align with the additional magnets of the other probe that are of the opposite polarity. As such, these types of additional magnets and ferromagnetic materials may be used as rotational alignment keys for an apparatus of an embodiment of the present invention.

In determining the type of magnets to be included in a probe, the weight of the magnets, the surface area of the magnets and the increased demagnetization effects attributable to the cylindrical length to diameter ratio and/or cylindrical length to radial width ratio of the magnet are typically taken into consideration. In this regard, magnets that are relatively thin and flat may have a substantial surface area so as to generate significant magnetic flux. However, these magnets are generally inefficient since they suffer from increased demagnetization effects due to their relatively small cylindrical length to diameter ratio and/or cylindrical length to radial width ratio relative to thicker, more rod-like ring magnets having a smaller surface area.

At least one of the probes 14, 16, usually the driven probe 14, includes a sensing element 132 for inspecting the structure 12 as the probe is moved over the respective surface of the structure. Further with respect to FIGS. 2, 3, and 4, the sensing element 132 is advantageously disposed or positioned in the center of a ring magnet 118 of a probe, such as affixed within a central cavity 140 of a housing 124. A sensing element may be a camera, an x-ray detector, pulse echo sensor, or the like, but generally is an ultrasonic transducer, such an ultrasonic transmitter and/or an ultrasonic receiver, for ultrasonically inspecting the structure as the probe is moved over the respective surface of the structure. For example, the ultrasonic transducer may be a 1 MHz immersion transducer from Agfa/Krautkramer of Lewistown, Pa.

Such probes provide for through transmission ultrasonic (TTU) inspection. Ultrasonic signals are transmitted into the structure by the ultrasonic transducer of one probe and received by the ultrasonic transducer of the other probe to detect flaws, including cracks, voids and/or porosity. However, only one probe needs to include a sensing element 32, 132 for inspection from one side of the structure 12. For example, one of the probes may include an ultrasonic transducer that is operated in a reflection or pulse echo mode. Thus, the same ultrasonic transducer both transmits and receives ultrasonic signals in this exemplary alternative embodiment. As another alternative example, the sensing element may be a camera that captures images of the respective surface of the structure from one side thereof. In these alternative embodiments, therefore, the probe that does not include a sensing element effectively serves to magnetically attract the probe with the sensing element to the respective surface of the structure. In the embodiments described, however, both the driven and tracking probes include a respective sensing element, such as an ultrasonic transducer.

A probe of an embodiment of the present invention may also include a housing 124 in which a magnet 118 and the sensing element, such as an ultrasonic transducer, are disposed and/or retained. The housing may be constructed of various non-magnetic materials and, in one embodiment, is constructed of Dehrin® material available from E.I. DuPont Nemours and Company of Wilmington, Del.

To facilitate the coupling of ultrasonic signals between ultrasonic transducer(s) of the driven and/or tracking probes 14, 16 and the structure 12, a couplant may be used. While air or water jets may be used as a couplant, the driven and/or tracking probes 14, 16 and, in particular, the respective housings may include an inlet 122 for a liquid, such as water, that is pumped between an ultrasonic transducer and a respective surface 12a, 12b of the structure. Fluids may be used as a couplant to provide a coupling path for the ultrasound signals between a transducer and a structure. Liquids such as water are particularly well suited to decrease the density differential between the transducer, air, and the surface of the structure. Gases such as air may be used as couplants, but typically require use of lower frequency ultrasonic signals. Because of the increased effectiveness of water as a couplant, air has not traditionally been used as a couplant for through-transmission ultrasonic inspection. While ambient pressure gases may be used as couplants, pressurized gases provide improved coupling paths and provide increased signal-to-noise ratios than non-pressurized gases for non-contact or airborne ultrasonic transducers; thus, for example, the pressurized air of an air bearing is a better couplant than ambient air. Increasing the pressure of the gas reduces the transfer loss at the interfaces at the transducer and surface of the structure allowing higher inspection frequencies. A waterless, non-contact or airborne, through-transmission ultrasonic transducer may be used with air or pressurized air. Also, a pressure control valve with a bleed value may be used to maintain a constant pressure for an air bearing, or other gas bearing. Improved flaw resolution may be obtained by using improved couplants. For example, the signal-to-noise ratio increases and the ultrasonic frequency may be increased. Both of these improvements, associated with increased fluid pressure, result in improved flaw resolution than would normally be obtained by non-pressurized couplants such as ambient air between a transducer and a structure.

Figure 2:
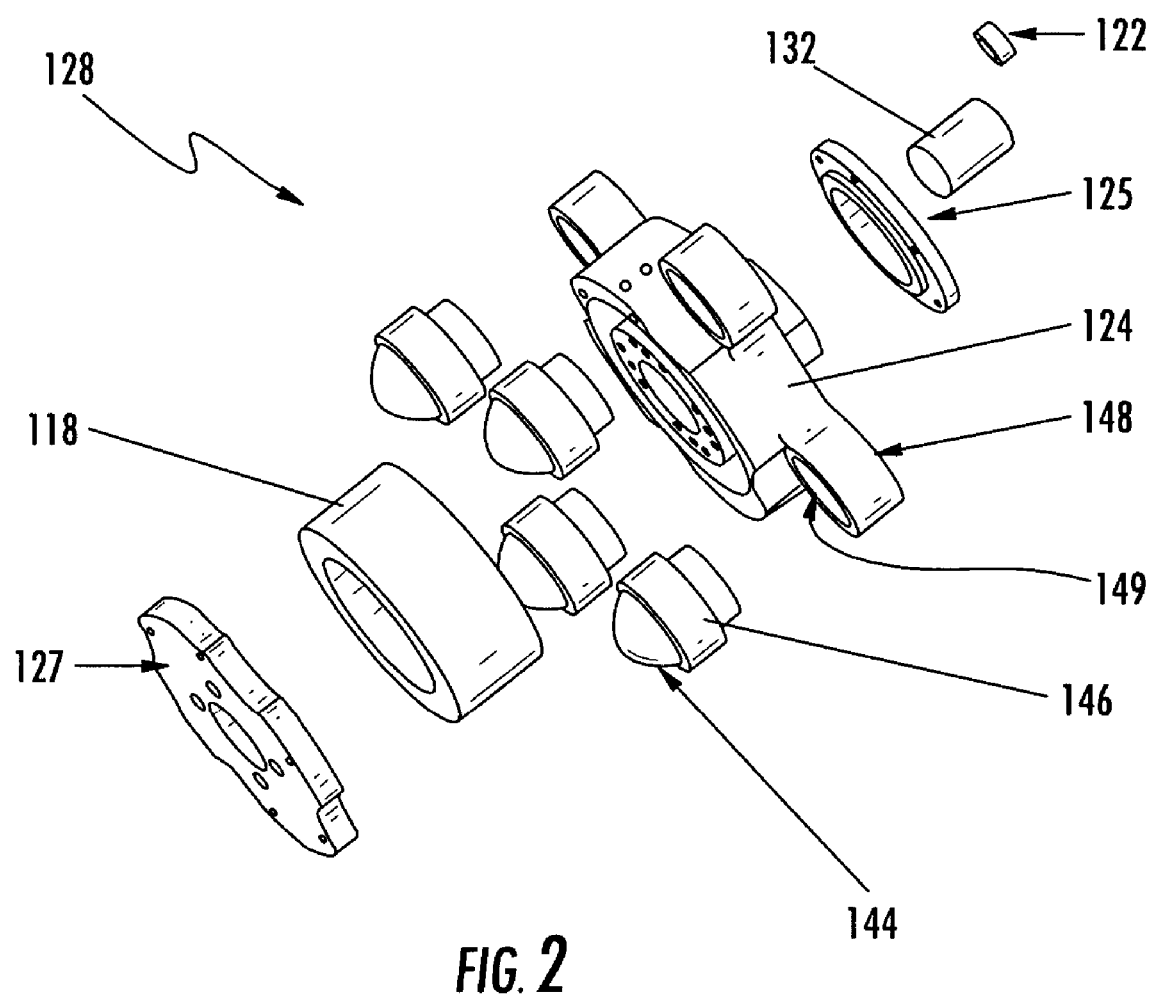
FIG. 2 is a bottom perspective view of an exploded diagram of a probe according to another embodiment of the present invention including ball and socket contact members.
Figure 3:
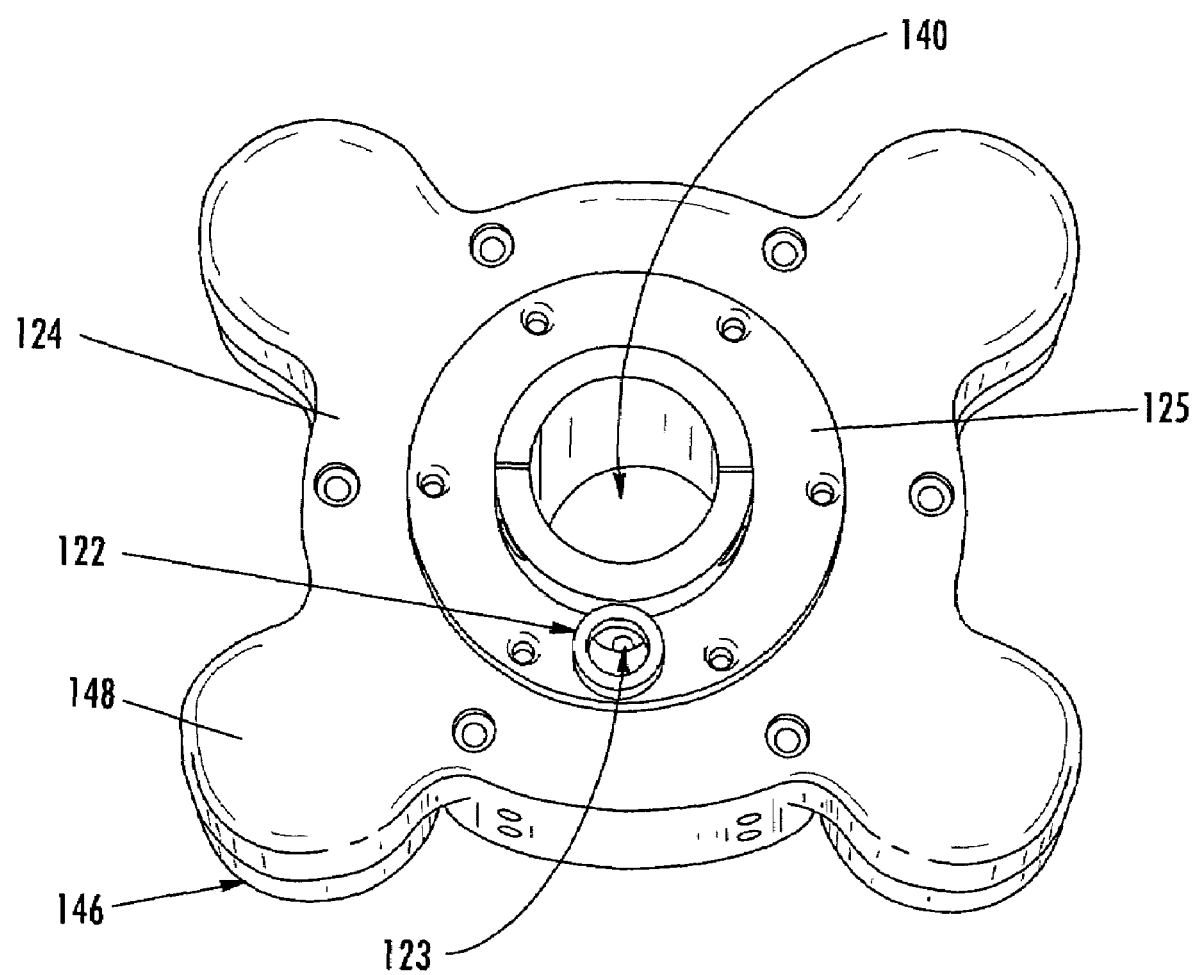
FIG. 3 is an overhead perspective view of a probe according to an embodiment of the present invention.
Figure 4:
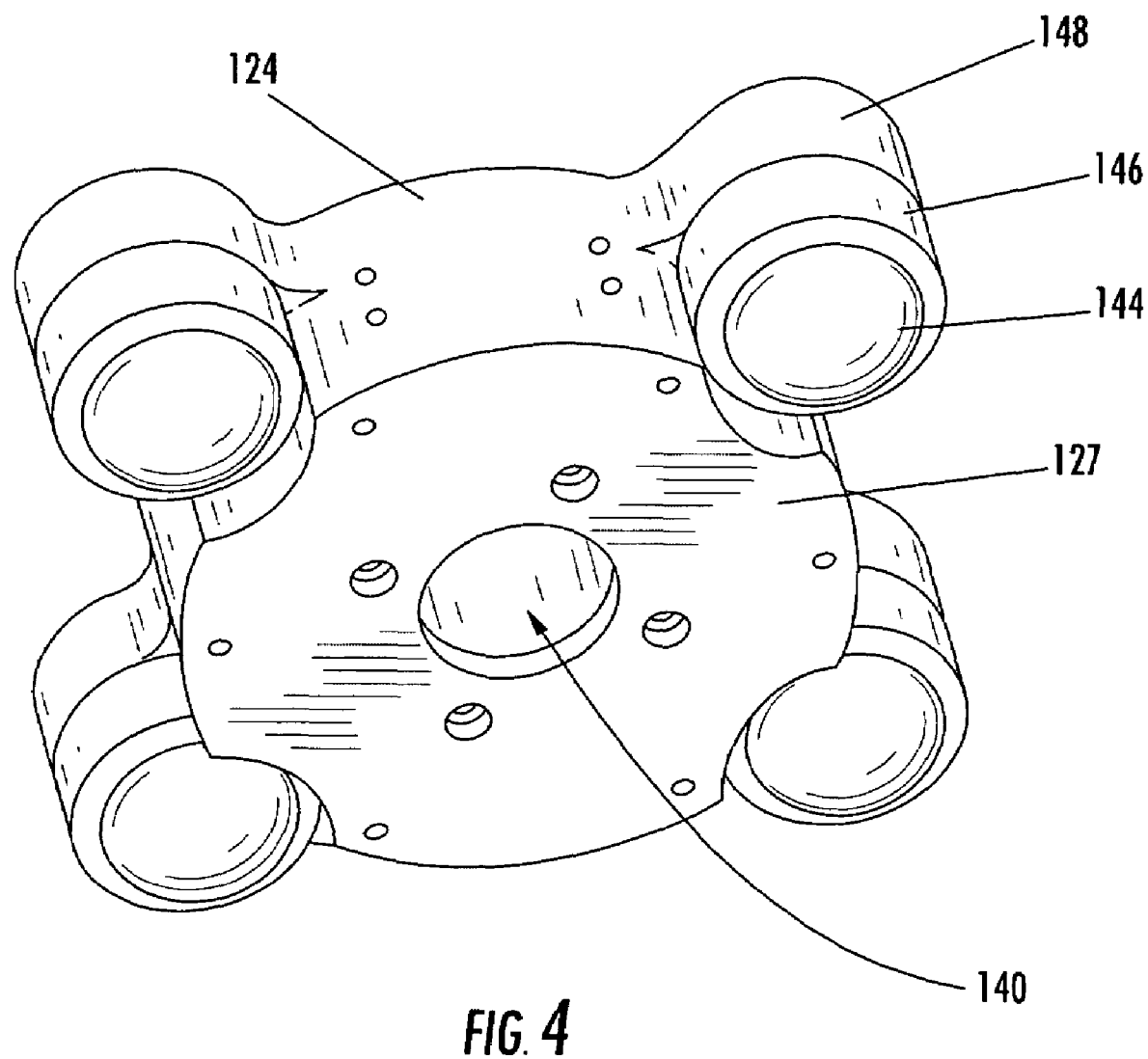
FIG. 4 is a bottom perspective view of a probe according to an embodiment of the present invention.

As shown in FIGS. 2, 3, and 4, the housing 124 includes one or more fluid inlets 122. The fluid inlet 122 may be in fluid communication with a portion of the sensing element 132, such as an ultrasonic transducer, that faces a surface of the structure 12 proximate the probe. The sensing element 132, such as an ultrasonic transducer, may be recessed within the housing 124. Thus, fluid that is introduced through the inlet 122 flows through the housing 124 and effectively fills the gap between the ultrasonic transducer and the surface of the structure 12. Advantageously, the fluid flows smoothly over and between the ultrasonic transducer and the surface of the structure with no bubbles, cavitation or turbulence that could otherwise detrimentally affect the signal to noise ratio. The shape and size of the housing does not dictate the present invention, but may be adapted to incorporate or facilitate features of the present invention. For example, the shape and size of the housing 24 shown in FIGS. 2A and 2B are dictated to provide support for the ring magnet 18 and fluid inlets 22. The shape is further dictated to provide smooth edges which may be proximate a surface of a part to avoid the housing interfering with the operation of embodiments of the present invention.

The fluid is supplied from a reservoir connected to the inlet 122. A tube press fit around the inlet 122 leads to a flow control valve. A flow control valve, also referred to as a pressure control valve, may be used to control the flow of fluid through the inlet 122, such as to control the flow of fluid based upon a measured fluid volume or pressure. A flow control valve may be located proximate the inlet 122 or may be in fluid communication with the inlet 122, such as where the flow control valve is located proximate the fluid source and controls the flow of fluid through tubes to the inlet 122. By positioning a flow control valve remote from an inlet prevents adding additional weight and complexity to the probe. A flow control valve or an inlet 122 may include a bleed to maintain constant pressure and prevent excess pressure or volume of fluid.

FIG. 2 is a perspective view of an exploded diagram of a probe according to an embodiment of the present invention including ball and socket bearings as seen from the side and below in the exploded diagram. A housing 124 may include a central cavity 140 to retain a sensor (not shown) such as an ultrasonic transducer. The embodiment of FIG. 2 has an inverted compressed housing 124, disposed around a ring magnet 118, with two caps 125, 127 and ball and socket bearings 128. Alternatively, a ring magnet may be retained in a housing with a cap integrally formed by the housing or with a recess for the ring magnet such that the housing does not require a cap or caps to retain the ring magnet. The ball and socket bearings 128 may include spherical bearings 144 each recessed into and housed by a socket 146. The sockets 146 may be attached to the housing or may be integrally connected to and formed by the housing. If the sockets may be removed from the housing, the ball and socket bearings 128 may be exchanged, such as after a spherical ball is worn due to extended use or to use a different type of ball for a different structure surface. If the sockets may be exchanged, sockets that retain different sizes of balls may be used for a single housing, such as where different sizes of ball bearings are desired for different structure surfaces. Similarly, if the balls may be removed from the respective sockets that are formed by the housing, the balls may be exchanged for new, different, or replacement balls. In one embodiment of the present invention, three or more spherical balls are held in three or more corresponding separate sockets to facilitate the rolling inspection of two magnetically attracted probes on opposite surfaces of a structure. The probes are capable of rolling across the surface of the structure under test.

FIG. 3 is a perspective view of a probe according to an embodiment of the present invention as seen from above the probe. FIG. 4 is a perspective view of the probe as seen from below the probe, from the surface side of the probe. The housing 124 includes a collar defining a central cavity 140 for holding a sensor such as an ultrasonic transducer. The housing 124 also includes an outer perimeter in which the sockets 146 are integrally formed and into which respective balls 144 may be inserted. Between the outer perimeter and central collar of the housing 124 is disposed a ring magnet. A first cap 125 and a second cap 127 secure the ring magnet within the housing 124. A fluid inlet 122 permits the flow of fluid through the inlet and the housing. In a ball bearing embodiment of the present invention, fluid such as water may be used as a couplant between an ultrasonic transducer and the surface of the structure being inspected. An inlet may be part of a fluid conduit that permits the flow of fluid through the housing.

Figure 5:
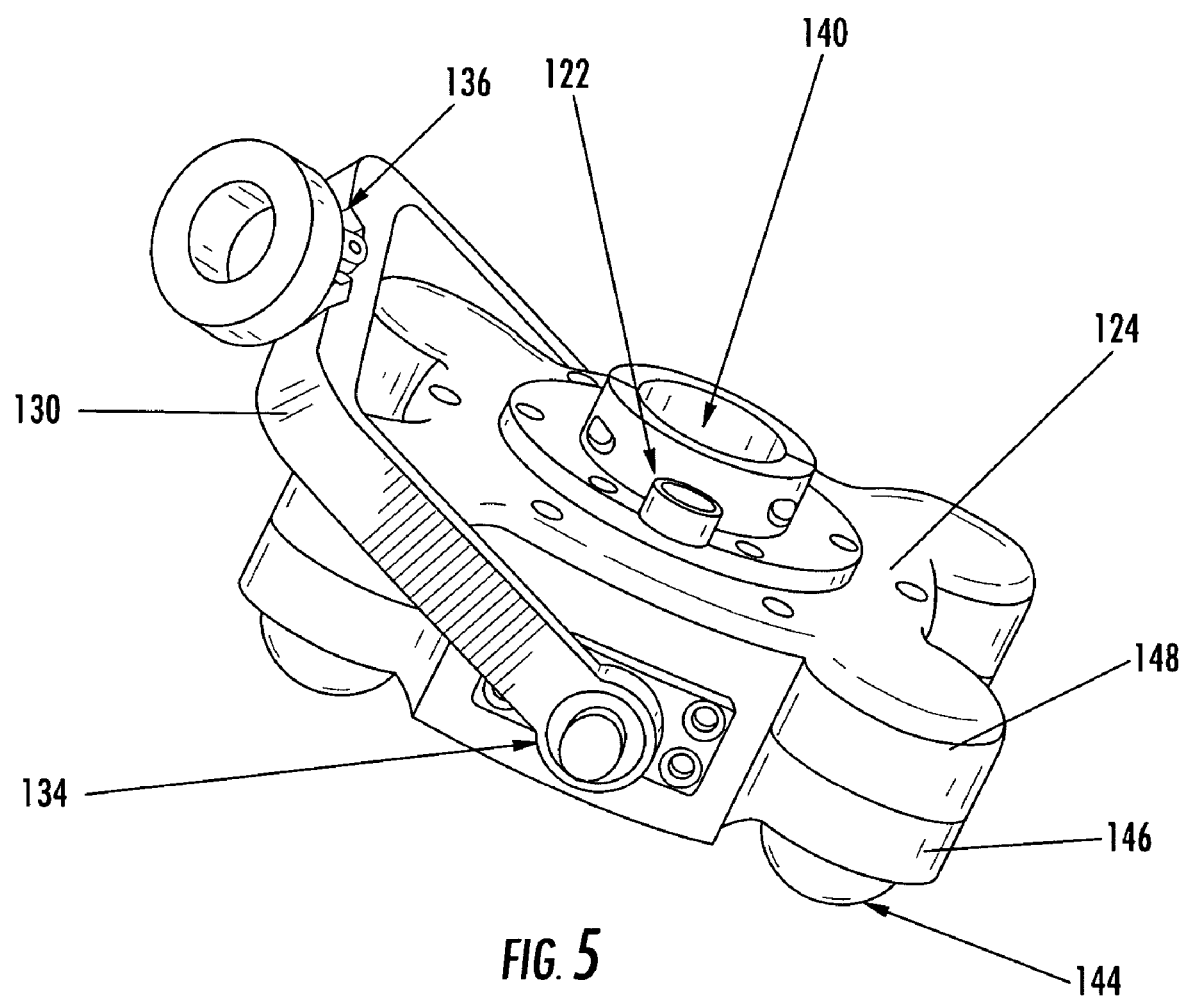
FIG. 5 is a perspective view of a probe according to an embodiment of the present invention including a yoke attachment.

FIG. 5 is a perspective view of a probe according to one embodiment of the present invention including a yoke attachment. A probe may include, or have attached, a handle or other connector, such as a yoke attachment 130, for controlling and driving the probe across a surface of a part. For example, a yoke attachment for embodiments of the present invention may include at least two points to provide multi-axis rotation of an inspection probe. The yoke attachment 130 may include hinge pivots 134 on either side of a housing and at a point 136 above the housing connecting to each of the side pivots 134. Alternatively or additionally, a rotating pivot (not shown) may be included at a point above the housing connecting to each of the side pivots 134. An attachment for an embodiment of the present invention may be gimbaled to permit the probe to remain in a magnetically coupled position regardless of the axes of motion of a connection providing movement of the probe across the surface of a structure under inspection. The described yoke attachment and similar handles and/or connectors enable inspection of parts with significant contours, including where a handle or connector is attached to a manual lever or robotic arm fixed to a control system for the robotic arm. Because the probes of embodiments of the present invention are magnetically attached, only a driven probe need be controlled, such as attached to or held by a yoke.

In operation, the driven and tracking probes 14, 16 are disposed proximate the first and second surfaces 12a, 12b of the structure 12. As shown in FIGS. 1A and 1B, the driven and tracking probes may advantageously be disposed in ball bearing contact with the respective surfaces of the structure. Ball bearing contact may provide suspension of a probe above a surface of a structure. Typically, the ball and socket bearings extend outwardly from the face or surface of the housing 124 that faces the respective surface of the structure. Ball bearings may be used to reduce the fiction between the inspection probe and the surface of the structure under inspection, such as to displace the probe from contacting the surface of the structure. Further, use of ball bearing contact between the inspection probe and the surface of the structure may avoid any undesirable damage or other marring of the respective surfaces of the structure as the result of contact with the probes, such as to prevent scratching of soft skins or denting of panels of the skins. Use of ball bearing contact may also provide smooth translation of an inspection probe over the surface of a structure to allow an inspection probe to maintain an intended direction, maintain alignment of transducers and/or receivers in inspection probes, and allow continuous scanning of a surface regardless of size, smoothness, or flatness of the surface.

By permitting ball bearing contact between the driven and tracking probes 14, 16 and the respective surfaces 12a, 12b of the structure 12, and by the magnetic attraction between the ring magnets of the probes, the orientation and alignment of the probes and, more particularly, the sensing elements, such as the ultrasonic transducers, of the probes may generally be maintained without requiring the orientation of the probes to be controlled by means of a complex motion control system or other type of positioning system. Additionally, the ball bearing contact between the driven and tracking probes and the respective surfaces of the structure may similarly maintain a consistent spacing between the respective sensing elements, such as the respective ultrasonic transducers, and the structure, without requiring complex motion control systems or other positioning systems. Further, the use of magnetically attracted inspection probes of embodiments of the present invention permit continuous scanning techniques such as manual scanning of an entire surface by comparison to point-by-point or grid-type inspection methods that may commonly be used for manual, semi-automated, and automated scanning systems. Because magnetically attracted probes maintain alignment of the transducers, an inspection area may be as large as the entire structure and a single operator may be able to inspect the structure. Enabling inspection of an entire structure rather than discrete points or areas for inspection improves the ability to detect imperfections in the structure and ensure structural integrity of a part.

Embodiments of the present invention may be scaled and adapted to be driven by a MAUS or AUSS system or other automated or semi-automated system or used as a manual inspection tool. For example, a yoke attachment to a magnetically attracted scanning probe may be connected to a MAUS or AUSS scanning bridge for in-service through-transmission ultrasonic inspection of a composite sandwich structure. This type of arrangement enables C-scan images of in-service TTU inspection data, such as using a MAUS system.

The operation of the apparatus 10 of the present invention will now be described in conjunction with driven and tracking probes 14, 16 configured to conduct a through transmission ultrasonic inspection. However, the driven and tracking probes may be used in other manners as described below. By way of example of the operation of one embodiment of the driven and tracking probes, however, the driven and tracking probes are disposed proximate to and generally in contact with the opposed first and second surfaces 12a, 12b of a structure 12 while maintaining alignment and magnetic attraction between the probes. Fluid, such as water, may then be bubbled through the inlet 122 of each probe and between the ultrasonic transducers and the respective surfaces 12a, 12b of the structure 12. Ball bearings may be used to maintain adequate spacing between the probe and the surface of the part under inspection. In such a manner, the ball bearings may be used to prevent the probe from contacting and possibly damaging the surface of the part. Further, the ball bearings provide the probe the ability to translate along the surface of the part for continuous scanning. The ultrasonic transducers are activated such that the ultrasonic transducer of one probe, such as the driven probe 14, emits ultrasonic signals into the structure. Although not shown, a drive element, such as a voltage or current source, is generally associated with the ultrasonic transducer of the driven probe so as to actuate the ultrasonic transducer to emit the ultrasonic signals. This drive element may be co-located with the driven probe or may be remote therefrom and electrically connected to the ultrasonic transducer. Correspondingly, the ultrasonic transducer of the other probe, such as a tracking probe 16, receives the ultrasonic signals originally transmitted by the ultrasonic transducer of the driven probe following the propagation of the ultrasonic signals through the structure.

While the ultrasonic signals are transmitted through the structure 12 and fluid is passed over the respective ultrasonic transducers, the driven probe 14 is moved along the first surface 12a of the structure. While the motive force required to move the driven probe along the first surface of the structure may be applied in various manners, the driven probe of the illustrated embodiment includes a handle 130 that may be engaged by a robotic arm or the like. As known to those skilled in the art, a robotic arm can be controlled by a motion control system or other positioning system so as to controllably move the driven probe in a predefined manner and in accordance with a defined pattern along the first surface of the structure. Since the driven probe is in contact with and rides along the first surface of the structure, the motion control system or other positioning system need not be as complex as that required by conventional scanning systems. By way of comparison to the AUSS-X system that requires a motion control system capable of controllably positioning the probes about ten axes, the motion control system used in conjunction with the apparatus 10 need only control the probes in five axes.

As a result of the magnetic attraction established between the driven and tracking probes 14, 16 and, more particularly, between the magnets 18 of the driven and tracking probes, the tracking probe moves in a like manner and in correspondence with the driven probe without requiring the application of any additional motive force directly to the tracking probe. Thus, the tracking probe moves so as to remain in an aligned, opposed position relative to the driven probe as the driven probe is moved along the first surface 12a of the structure 12. As such, the tracking probe need not be engaged by a robotic arm or other positioning system. Accordingly, the tracking probe can be disposed proximate to and can ride along a second surface 12b of a structure that is relatively inaccessible, such as the interior of a cylindrical structure or other structure having a closed shape.

The ultrasonic signals that are received by the ultrasonic transducer of the tracking probe 16 can be stored along with an indication of the time at which the ultrasonic signals are received and/or an indication of the relative position of the tracking probe when the ultrasonic signals are received. The ultrasonic signals may be stored by a memory device that is either co-located with the tracking probe or remote from the tracking probe and electrically connected therewith. By analyzing the ultrasonic signals received by the ultrasonic transducer of the tracking probe, the integrity of the structure 12 as well as any flaws therein can be determined.

By passing fluid between the ultrasonic transducer and the respective surface of the structure 12, the ultrasonic signals are effectively coupled into and out of the structure in one advantageous embodiment. Moreover, while a single ultrasonic transducer is depicted in FIG. 2, the driven and/or tracking probes 14, 16 may include an array of ultrasonic transducers to increase the inspection area since the coupling provided by the fluid permits inspection in an ultrasonic array mode, thereby increasing the speed with which the inspection is performed and correspondingly reducing the cost associated with the inspection.

A tracking probe may include a larger diameter transducer than the transducer of a driven probe. Using a larger tracking probe transducer enables a more uniform signal over a larger area than would a corresponding smaller transducer. Thus, using a larger tracking probe transducer may minimize the effect of small misalignments between the driven probe and tracking probe, and transducers thereof, such as misalignments due to discontinuities in the surfaces of the structure, positional lagging of the tracking head, and gravitational offset.

II. Water Column Skirt

A fluid, such as water or another liquid, may be used as a couplant between an ultrasonic transducer and the surface of the part under inspection. Using a couplant may help to achieve higher resolution inspection imaging of the part under inspection on a structure that can be wetted by permitting the use of higher frequency inspection signals. A water column skirt may be employed to maintain coupling such as to form a coupling path between the ultrasonic transducer and the surface of the part to permit good coupling from the transmitting transducer through a part under inspection. Use of a water column skirt is advantageous where the ball bearings require the probe to be held apart from the surface of the part, creating a separation between the probe and the surface of the part into and through which a couplant may disperse from the probe. Also, by using a water column skirt, an embodiment of the present invention may be able to use a lesser volume of couplant than if a water column skirt is not used. Accordingly, the couplant may be bubbled or dribbled in lower volume, at a low flow level, through the probe and continue to maintain a coupling path between the ultrasonic transducer and the surface of the part, as the couplant flows out slowly from under the water column skirt. Further, by using a water column skirt, coupling may be maintained with surfaces that exhibit contours, roughness, and other surface discontinuities. Water may be replaced with any suitable fluid which provides a coupling path between a transducer and a surface of a structure under inspection.

Figure 6:
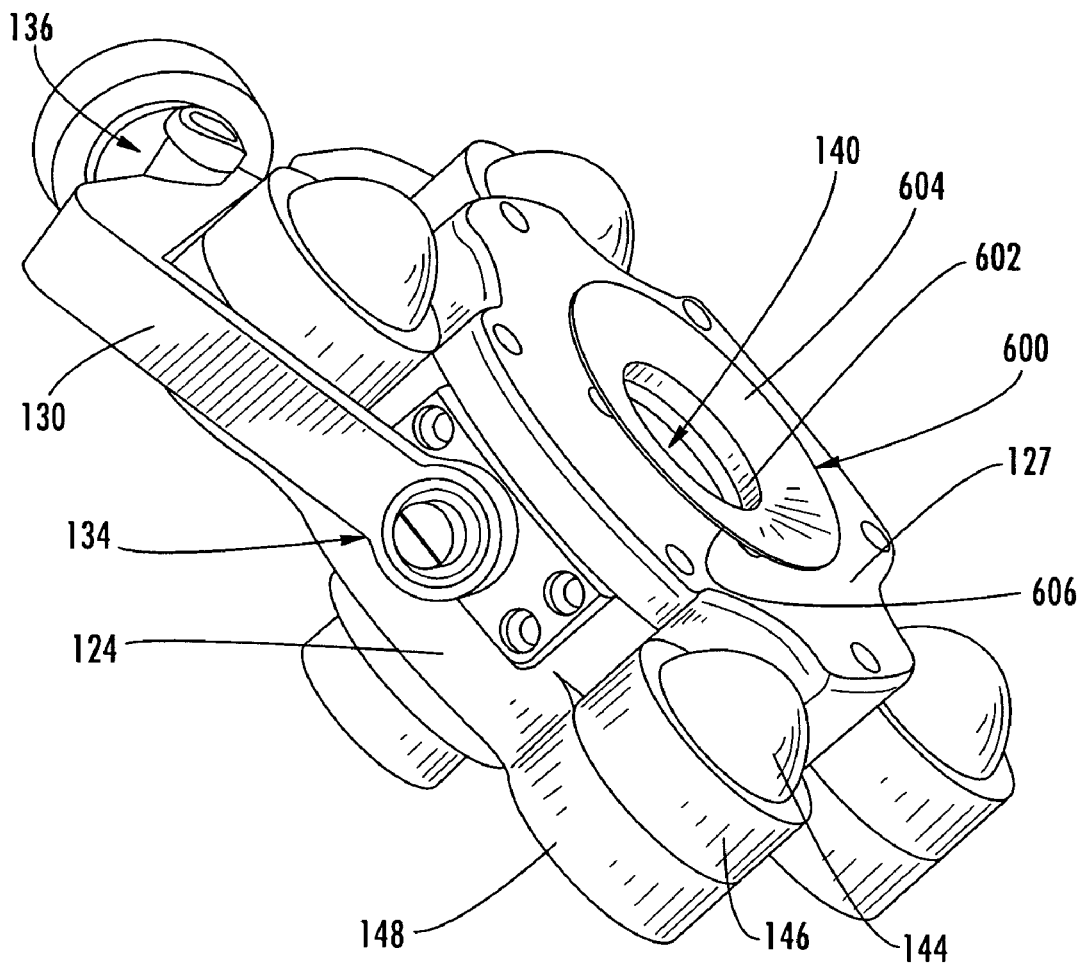
FIG. 6 is a bottom perspective view of a probe employing a water column skirt according to an embodiment of the present invention.
Figure 7:
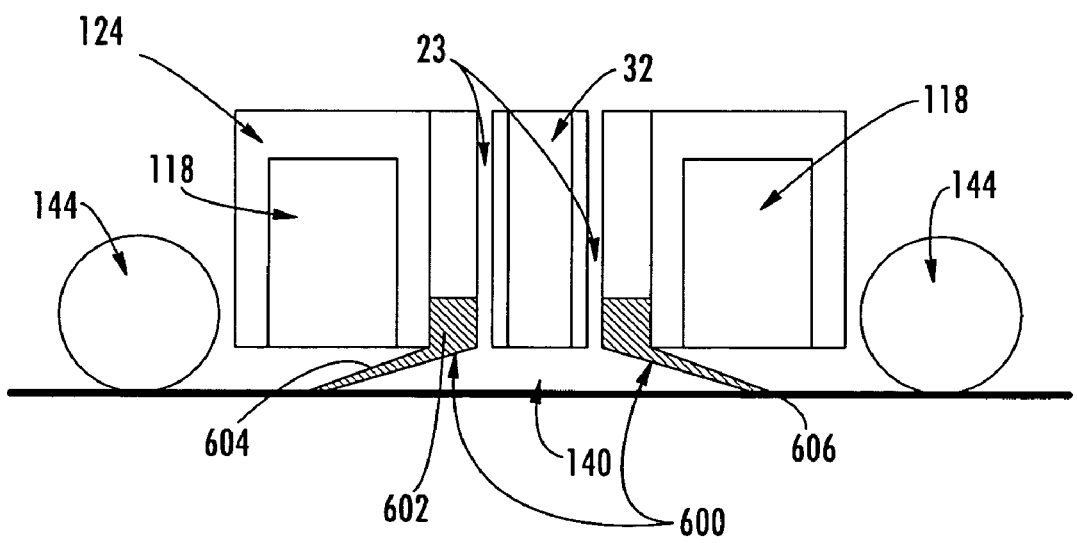
FIG. 7 is a schematic diagram of a probe employing a water column skirt according to an embodiment of the present invention.

FIG. 6 is a perspective view of a probe employing a water column skirt. FIG. 7 is a schematic diagram of the probe of FIG. 6. A water column skirt 600 may be a flexible cowling which floats over the surface of the part and holds a couplant, such as water or another liquid, in a column to create a path between an ultrasonic transducer and the surface of a part under inspection. A water column skirt may be formed from a pliable, Teflon® structure or other material in accordance with an embodiment of the present invention. A cap 127 may be formed to permit a water column skit 600 to mount to the bottom surface of the probe, the surface of the probe adjacent to the surface of the structure under inspection. A water column skirt 600 may be formed with a short, cylindrical tube 602 encircling the transducer 32 within a central cavity 140 of the probe and encircling fluid channels 23 opening on the bottom surface of the probe. A water column skirt 600 may be further formed from a flared, tapered, flexible skirting 604 projecting radially outwardly from the cylindrical tube 602 and downwardly from the probe towards the surface of the structure under inspection. A water column skirt may be shaped and made from materials selected to allow the water column skirt to advantageously flex to adjust for contour changes and other surface discontinuities on the surface of the structure under inspection. For example, a water column skirt may be made of low-friction substance, such as Teflon® or the like, to facilitate smooth translation of the probe over a surface of a part, such as to permit a lip 606 of the flared skirting 604 of the water column skirt 600 to translate over the surface of a structure under inspection with a minimum of frictional drag. As can be seen in FIG. 7, only the lip 606, and any surface material coating thereof such as a low-friction substance, such as Teflon® or the like, of the flared skirting 604 of the water column skirt 600 may contact the surface of the structure under inspection. Further a water column skirt may be shaped and formed from materials selected to allow the water column skirt to advantageously hold a column of couplant between a face of an ultrasonic transducer and the surface of the structure under inspection. For example, a water column skirt should be made from a material stiff enough to support the pressure of a couplant column.

If water, or another liquid, is used with an embodiment of the present invention, the probe or apparatus will likely include or be used with a reservoir to collect the expelled water and, possibly, recycle the water. For example, if water is used as a couplant, the water that spills or drains off of a part may be collected and recycled to be used again as a couplant. Similarly, if a pressurized gas is used, a reservoir such as a containment housing, a sealed room, or the like, may be used to capture and recycle the gas, or possibly to maintain a constant pressure for the gas being used. For example, if an oxygen enriched air mixture or other gaseous mixture, such as a composition of 35% oxygen ($O_2$), 63.5% nitrogen ($N_2$), 1% argon (Ar), and 0.5% carbon dioxide ($CO_2$) with trace amounts of neon (Ne), helium (He), methane ($CH_4$), etc., is found to increase coupling of an ultrasonic signal and, therefore, used as a couplant, a sealed chamber may be used to surround the structure being inspected and the probes such that the oxygen enriched air mixture may be present in the sealed chamber and may be pumped through the probe to be used as a pressurized gas couplant. Various considerations may impact a selection of a couplant, such as whether internal systems of a structure can be exposed to a fluid such as water, the availability of a fluid, and the difficulty to maintain, collect, and/or recycle a fluid. Similar considerations may impact the selection of the type of inspection method or sensor to be used. For example, non-contact air ultrasonic transducers typically require lower frequency signals compared to water-coupled ultrasonic transducers. Thus, although water may be a better couplant than air, a system using pressurized air as a couplant may be selected to eliminate the complications associated with using water with an inspection system. An embodiment of the present invention may use one type of a bearing contact for the driven probe and the same or a different type of bearing contact for the tracking probe, such as where the tracking probe is located inside a part and proximate components which may not readily accept the presence of certain bearing contact such as a water bearing. For example, a driven probe may use a water couplant and a tracking probe may use an air couplant. Alternatively, the driven probe may use an air couplant and the tracking probe may use a water couplant. Regardless of the type of fluid selected for a couplant, the additional elements of a couplant such as hoses add weight to a probe, particularly water hoses which may make an air couplant more appropriate for some inspection situations.

Many modifications and other embodiments of the inventions set forth will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed, they are used in a generic and descriptive sense only and not for purposes of limitation.

The invention claimed is:

1. An apparatus for inspecting a structure comprising:
 a driven probe structured for traveling over a first surface of the structure, said driven probe comprising a magnet and a sensor for inspecting the structure as said driven probe is moved over the first surface of the structure; and
 a tracking probe structured for traveling over an opposed second surface of the structure, said tracking probe also comprising a magnet for cooperating with said magnet of said driven probe to draw the driven and tracking probes toward the first and second surfaces of the structure, respectively, wherein magnetic attraction between said driven and tracking probes causes said tracking probe to be moved over the second surface of the structure in response to corresponding movement of said driven probe, and wherein at least one of said driven probe and said tracking probe comprise at least one ball bearing between said respective probe and the surface of the structure.

2. The apparatus of claim 1, wherein said magnet of said driven probe is a ring magnet, and wherein said sensor of said driven probe is disposed within said ring magnet.

3. The apparatus of claim 2, wherein said magnet of said tracking probe is a ring magnet.

4. The apparatus of claim 3, wherein said ring magnet of said driven probe and said ring magnet of said tracking probe are different sizes.

5. The apparatus of claim 3, wherein said tracking probe further comprises a sensor disposed within said ring magnet of said tracking probe for receiving signals from said sensor of said driven probe.

6. The apparatus of claim 5, wherein said sensor of said tracking probe and said sensor of said driven probe are ultrasonic transducers.

7. The apparatus of claim 5, wherein said sensor of said tracking probe has a larger inspection area than an inspection area of said sensor of said driven probe.

8. The apparatus of claim 1, wherein said magnet of said tracking probe is a ring magnet, and wherein said sensor of said tracking probe is disposed within said ring magnet of said tracking probe.

9. The apparatus of claim 8, wherein said tracking probe further comprises a sensor disposed within said ring magnet of said tracking probe for receiving signals from said sensor of said driven probe.

10. The apparatus of claim 8, wherein said sensor of said tracking probe and said sensor of said driven probe are ultrasonic transducers.

11. The apparatus of claim 1, wherein said sensor of said driven probe is an ultrasonic transducer.

12. The apparatus of claim 9, wherein said magnet of said driven probe is a ring magnet, and wherein said ultrasonic transducer is disposed within said ring magnet.

13. The apparatus of claim 1, wherein at least said driven probe comprises a fluid inlet to provide a couplant between said sensor and said first surface of the structure.

14. The apparatus of claim 13, further comprising a water column skirt disposed on said driven probe.

15. The apparatus of claim 14, wherein said water column skirt comprises a flexible cowling.

16. The apparatus of claim 14, wherein said fluid inlet comprises at least one fluid outlet channel, and wherein said water column skirt comprises:
 a cylindrical tube disposed around at least one of said fluid outlet channels of said fluid inlet; and
 a skirting projecting radially outwardly from said cylindrical tube and from said driven probe.

17. The apparatus of claim 16, wherein the distal edge of said skirting from said cylindrical tube and said driven probe comprises a low-friction substance.

18. The apparatus of claim 13, wherein said couplant is water.

19. The apparatus of claim 18, further comprising a water column skirt disposed on said driven probe.

20. The apparatus of claim 13, wherein said couplant is air.

21. A probe for inspecting a structure comprising:
 a housing;
 a ring magnet carried by said housing, wherein said ring magnet defines an inner cylindrical surface, and wherein said ring magnet is configured to be carried by said housing with a surface of the structure being inspected generally perpendicular to the inner cylindrical surface;
 at least one ball bearing supported by said housing and for contacting a surface of the structure being inspected; and
 a sensor disposed within said ring magnet, wherein said sensor is configured to inspect the surface of the structure being inspected that is positioned generally perpendicular to the inner cylindrical surface and such that the sensor is configured to employ an inspection path generally parallel to the inner cylindrical surface.

22. A probe for inspecting a structure comprising:
 a housing;
 a ring magnet carried by said housing;
 at least one ball bearing supported by said housing and for contacting a surface of the structure being inspected;
 a sensor disposed within said ring magnet; and
 a fluid inlet supported by said housing and wherein said fluid inlet is in fluid communication with said sensor for distributing fluid between said sensor and the surface of the structure being inspected to provide a coupling path for signals of said sensor.

23. The probe of claim 22, further comprising a flow control valve affixed to said fluid inlet to control the flow of fluid through said fluid inlet.

24. The probe of claim 23, wherein fluid flow is controlled by said flow control valve based upon at least one of fluid volume or fluid pressure.

25. The probe of claim 22, further comprising a water column skirt disposed on said housing, wherein said fluid inlet comprises at least one fluid outlet channel and said water column skirt is disposed around at least one of said fluid outlet channels.

26. The probe of claim 25, wherein said water column skirt comprises a flexible cowling.

27. The probe of claim 25, wherein said fluid inlet comprises at least one fluid outlet channel, and wherein said water column skirt comprises:
 a cylindrical tube disposed around at least one of said fluid outlet channels of said fluid inlet; and
 a skirting projecting radially outwardly from said cylindrical tube and said housing.

28. The probe of claim 27, wherein the distal edge of said skirting from said housing comprises a low-friction substance.

29. The probe of claim 21, further comprising an array of ultrasonic transducers, carried by said housing.

30. The probe of claim 21, wherein said probe comprises a plurality of at least three ball bearings.

31. A method of inspecting a structure comprising:
   supporting a driven probe on a first surface of the structure with at least one ball bearing and a tracking probe on an opposed second surface of the structure with at least one ball bearing;
   establishing magnetic attraction between the driven probe and the tracking probe such that the driven probe and the tracking probe are drawn toward the first and second surfaces of the structure, respectively;
   aligning the driven probe and the tracking probe using a ring magnet of the driven probe and a ring magnet of the tracking probe;
   rolling the driven probe along the first surface of the structure which causes the tracking probe to be correspondingly rolled along the second surface of the structure; and
   transmitting inspection signals into and receiving inspection signals from the structure as the driven probe is moved along the first surface of the structure and the tracking probe is correspondingly moved along the second surface of the structure.

32. The method of claim 31, further comprising the step of coupling inspection signals between at least one of the driven and tracking probes and the first and second surfaces of the structure, respectively.

33. The method of claim 32, wherein said step of coupling inspection signals comprises the step of pumping a fluid between the respective probe and the respective surface.

34. The method of claim 33, further comprising the step of controlling the flow of fluid pumped between the respective probe and the respective surface.

35. The method of claim 32, further comprising the steps of:
   passing a couplant between the respective probe and the respective surface; and
   creating a couplant column between the respective probe and the respective surface.

36. The method of claim 35, wherein said step of passing a couplant comprises the step of bubbling water.

* * * * *